(12) United States Patent
Higuchi et al.

(10) Patent No.: US 8,486,462 B2
(45) Date of Patent: *Jul. 16, 2013

(54) GLYCOSIDE HAVING 4-METHYLERGOST-7-EN-3-OL SKELETON AND HYPERGLYCEMIA IMPROVING AGENT

(75) Inventors: Ryuuichi Higuchi, Fukuoka (JP); Masanori Inagaki, Fukuoka (JP); Hirotoshi Hayasawa, Tokyo (JP); Muneo Yamada, Zama (JP); Miyuki Tanaka, Zama (JP); Eriko Misawa, Zama (JP); Noriko Wakimoto, Zama (JP); Yousuke Itou, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 795 days.

This patent is subject to a terminal disclaimer.

(21) Appl. No.: 12/180,241

(22) Filed: Jul. 25, 2008

(65) Prior Publication Data

US 2009/0075913 A1 Mar. 19, 2009

Related U.S. Application Data

(62) Division of application No. 10/564,464, filed as application No. PCT/JP2005/006019 on Mar. 30, 2005, now Pat. No. 7,534,770.

(30) Foreign Application Priority Data

Mar. 31, 2004 (JP) ................................. 2004-103684
Apr. 6, 2004 (JP) ................................. 2004-112108

(51) Int. Cl.
*A61K 36/886* (2006.01)
*A61K 36/00* (2006.01)

(52) U.S. Cl.
USPC .......................................... 424/744; 424/725

(58) Field of Classification Search
None
See application file for complete search history.

(56) References Cited

U.S. PATENT DOCUMENTS

| | | | |
|---|---|---|---|
| 4,598,069 A | 7/1986 | Hikino et al. | |
| 6,506,387 B1 * | 1/2003 | Cohen | 424/744 |
| 2003/0207818 A1 | 11/2003 | Jia et al. | |

FOREIGN PATENT DOCUMENTS

| | | |
|---|---|---|
| JP | 60-214741 | 10/1985 |
| JP | 01-312978 | 12/1989 |
| JP | 05-247086 | 9/1993 |
| JP | 406319498 A * | 11/1994 |
| JP | 08-208495 | 8/1996 |
| JP | 09-040689 | 2/1997 |
| JP | 09-059298 | 3/1997 |
| JP | 09-070278 | 3/1997 |
| JP | 09-224588 | 9/1997 |
| JP | 10-036271 | 2/1998 |
| JP | 10-036283 | 2/1998 |
| JP | 10-045604 | 2/1998 |
| JP | 10-120576 | 5/1998 |
| JP | 10-330266 | 12/1998 |
| JP | 11-511482 | 10/1999 |
| JP | 2001-520019 | 10/2001 |
| JP | 2002-205949 | 7/2002 |
| JP | 2002-371003 | 12/2002 |
| JP | 2003-048837 | 2/2003 |
| JP | 2003-095941 | 4/2003 |
| JP | 2003-286185 | 10/2003 |
| WO | WO 97/16438 | 5/1997 |
| WO | WO 99/19505 | 4/1999 |
| WO | WO 03/059360 | 7/2003 |

OTHER PUBLICATIONS

DW ACC 2003-808158, Aug. 2003, DW or JP2003238, Hasebe et al.*
Akihisa, et al. "Triterpene Alcohols and Sterols from the Fern *Gleichenia japonica* Spr.," *Chem. Pharm. Bull.*, vol. 41, No. 3, pp. 624-626, 1993.
Nes, "Sterol Methyl Transferase: Enzymology and Inhibition," *Biochimica et Biophysica Acta*, vol. 1529, pp. 63-88, 2000.
Bunyapraphatsara, et al. "Antidiabetic Activity of *Aloe vera* L. Juice II. Clinical Trial in Diabetes mellitus Patients in Combination with Glibenclamide," *Phytomedicine*, vol. 3, No. 3, pp. 245-248, 1996.
Okyar, et al. "Effect of *Aloe vera* Leaves on Blood Glucose Level in Type I and Type II Diabetic Rat Models," *Phytotherapy Research*, vol. 15, pp. 157-161, 2001.
Beppu, et al. "Hypoglycaemic and Antidiabetic Effects in Mice of *Aloe arborescens* Miller var. *natalensis* Berger," *Phytotherapy Research*, vol. 7, pp. S37-S42, 1993.
Nippon Rinsho, No. 748, vol. 1, pp. 615-617, 1999 with a partial English translation.
Nippon Rinsho, No. 808, vol. 2, pp. 405-409, 2002 with a partial English translation.
Yazaki Y. & Muramatsu M. Ed., "Front Line of Diabetes mellitus," pp. 126-139, Yodosha, 1997 with a partial English translation.
Panosyan, et al. Khymiya Prirodmykh Soedinenii, vol. 3, USSR, 1977, Caplus/Medline Abstract.
Yongchaiyudha, et al. "Antidiabetic Activity of *Aloe vera* L. Juice.I. Clinical Trial in New Cases of Diabetes mellitus," *Phytomedicine*, vol. 3, No. 3, pp. 241-243, 1996.
Koo, "Aloe Vera, Antiulcer and Antidiabetic Effects," *Phytotherapy Research*, vol. 8, pp. 461-464, 1994.
Akihisa T., Matsumoto T., Yukagaku, vol. 36, pp. 301-319, 1987 with a relevance explanation.
Can, et al. "Effect of *Aloe vera* Leaf Gel and Pulp Extracts on the Liver in Type-II Diabetic Rat Models," *Biol. Pharm. Bull.* vol. 27, No. 5, pp. 694-698, 2004.

(Continued)

*Primary Examiner* — Michele Flood
*Assistant Examiner* — Randall Winston
(74) *Attorney, Agent, or Firm* — Knobbe, Martens, Olson & Bear LLP

(57) ABSTRACT

3-O-β-D-Glucopyranosyl-4-methylergost-7-en-3-ol or a composition containing 0.001% by mass or more of the aforementioned compound, which is an extract of a plant of the family Liliaceae containing the compound or a fraction thereof, is used as an active ingredient of a hyperglycemia improving agent.

3 Claims, 4 Drawing Sheets

OTHER PUBLICATIONS

Yeh, et al. "Systematic Review of Herbs and Dietary Supplements for Glycemic Control in Diabetes," *Diabetes Care*, vol. 26, No. 4, pp. 1277-1294, 2003.

Afzal, et al. "Identification of Some Prostanoids in *Aloe vera* Extracts," *Planta Med.*, vol. 57, pp. 38-40, 1991.

Ghannam, et al. "The Antidiabetic Activity of Aloes: Preliminary Clinical and Experimental Observations," *Hormone Res.*, vol. 24, pp. 288-294, 1986.

Ajabnoor, "Effects of Aloes on Blood Glucose Levels in Normal and Alloxan Diabetic Mice," *Journal of Ethnopharmacology*, vol. 28 pp. 215-220, 1990.

Grover, et al. "Medicinal Plants of India with Anti-Diabetic Potential," *Journal of Ethnopharmacology*, vol. 81, pp. 81-100, 2002.

Bolkent, et al. "Effect of *Aloe vera* (L.) Burm. fil. Leaf Gel and Pulp Extracts on Kidney in Type-II Diabetic Rat Models," *Indian Journal of Experimental Biology*, vol. 42, pp. 48-52, Jan. 2004.

Hikino, et al. "Isolation and Hypoglycemic Activity of Arborans A and B, Glycans of *Aloe arborescens* var. natalensis Leaves," *Int. J. Crude Drug Res.*, vol. 24, pp. 183-186, 1986.

Yeh, et al. "Systematic Review of Herbs and Dietary Supplements for Glycemic Control in Diabetes," *Diabetes Care*, vol. 26, No. 4, pp. 1277-1294, Apr. 2003.

Abou-Zeid, "Chemical and Biological Study of the Leaves of some *Musa* Species," *Egypt. J. Pharm. Sci.*, vol. 39, Nos. 4-6, pp. 379-398, 1998.

Jamaluddin, et al. "Hypoglycaemic Effect of Stigmast-4-en-3-one, from *Parkia speciosa* Empty Pods," *Food Chemistry*, vol. 54, No. 1, pp. 9-13, Jan. 1, 1995.

Supplementary European Search Report dated Jun. 22, 2009.

* cited by examiner

GLYCOSIDE HAVING 4-METHYLERGOST-7-EN-3-OL SKELETON AND HYPERGLYCEMIA IMPROVING AGENT

RELATED APPLICATIONS

This application is a divisional of U.S. application Ser. No. 10/564,464, filed Jan. 12, 2006 which is the U.S. National Phase under 35 U.S.C. §371 of International Application PCT/JP2005/006019, filed Mar. 30, 2005, which was published in a language other than English, which claims priority of JP Application No. 2004-103684, filed Mar. 31, 2004 and JP Application No. 2004-112108, filed Apr. 6, 2004.

TECHNICAL FIELD

The present invention relates to a novel glycoside having a 4-methylergost-7-en-3-ol skeleton, 3-O-β-D-glucopyranosyl-4-methylergost-7-en-3-ol, a composition containing the same, a drug and food or drink containing these.

BACKGROUND ART

4-Methylergost-7-en-3-ol is known to be a substance that exists in plants (Non-patent document 1). As for prior arts of this compound, however, there is only a reference concerning the biosynthetic system of lophenol (one of the stereoisomers of 4-methylcholest-7-en-3-ol) having a structure similar to that of the aforementioned compound (Non-patent document 2), and the use of these compounds is not known at all.

The genus *Aloe* in the family Liliaceae is a group of plants including *Aloe vera* (*Aloe barbadensis* Miller) and *Aloe arborescens* (*Aloe arborescens* Miller var. *natalensis* Berger) and so forth, and they are empirically known to have various efficacies. The prior arts regarding the use of plants of the genus *Aloe* include immunomodulating polysaccharides (Patent document 1), immunosuppression improving agents containing a butanol fraction of an aloe extract or aloin (Patent document 2), HSP60 family protein synthesis suppressing agents containing aloin derivatives (Patent documents 3 to 5), proteins having lectin activity derived from aloe leaf-skin (Patent document 6) and so forth.

As the prior arts regarding improvement of blood glucose levels by the plants of the genus *Aloe*, clinical studies in the United States (Non-patent document 3) and a hypoglycemic action observed in animal studies (Non-patent documents 4 and 5) and polysaccharides in plants of the genus *Aloe* (Patent document 7) have been disclosed. In these prior arts, the hypoglycemic ingredients of the plants of the genus *Aloe* were predicted to be polysaccharides or glycoproteins. Furthermore, it has been disclosed that, in a pressed extract of *Aloe vera* and a hypoglycemic agent containing the extract as an active ingredient (Patent document 8), a characteristic peak unique to an ester group observed in the FT-IR chart correlates with the activity, that the active ingredient is a polysaccharide, amino acid, malic acid or the like, and that the aforementioned active ingredient is degraded in commercially available *Aloe vera* gel powders, *Aloe vera* gel solutions and *Aloe vera* gel extracts. Furthermore, in addition to the above, a hypoglycemic action of aloe polysaccharides (Patent document 9) and antioxidative action of 7-hydroxychromone contained in aloe (Patent document 10) have been disclosed.

Meanwhile, because *Aloe vera* leaf-skin contains barbaloin and aloe-emodin having a laxative action, it has been conventionally considered unfavorable for industrial use.

Hemoglobin A1c, a binding product of glucose and hemoglobin, increases depending on the severity of hyperglycemia in a glucose level-dependent manner. Because hemoglobin A1c once produced is not eliminated until the lifetime of erythrocyte (120 days) runs out, it reflects the past blood glucose control conditions over a long period of time (Non-patent document 6). Hemoglobin A1c was adopted as a selected test item of the basic health screening according to the Health Law for the Aged since 1996 and adopted as an auxiliary diagnosis indicator of diabetes mellitus in the new diagnosis criteria of diabetes mellitus in 1999. Therefore, it is considered that hemoglobin A1c is an indicator of great clinical significance (Non-patent document 7).

If a hyperglycemic condition is sustained, glucose specific insulin hyposecretion and insulin resistance are observed and serve as factors that further aggravate hyperglycemia (Non-patent document 8). Because long-term blood glucose level control is necessary to prevent progression from the hyperglycemic condition to onset of diabetes mellitus, it is considered to become necessary to suppress increase in the hemoglobin A1c level. Alimentotherapies and exercise are recommended to control blood glucose level in patients with prediabetes (likelihood of developing diabetes or related conditions). Although various functional foods for preventing postprandial increases in blood glucose level (food for specified health uses) have already been marketed, all of these only have a temporary effect of suppressing increase in blood glucose level. Therefore, control of blood glucose level over a long period of time cannot be expected, and development of such a substance having a hemoglobin A1c level lowering action as in the present invention has been desired.

Furthermore, α-glucosidase inhibitors, sulfonylurea drugs as insulin secretagogues, thiazolidine derivatives as insulin resistance improving agents and so forth are currently used as therapeutic agents for diabetes mellitus. However, the drug efficacies thereof are not satisfactory, and they suffer many problems such as side effects causing coma due to rapid drop in blood glucose level.

Under the aforementioned circumstances, discovery of a substance that can be safely ingested without causing acute hypoglycemia and has a long-term blood glucose level control action by decreasing the hemoglobin A1c level has been strongly desired.

Conventionally, as examples of substances having an effect of suppressing increases in blood glucose level, the prior art references have disclosed a hyperglycemia suppressing agent containing a banaba-derived ingredient (Patent document 11), a hyperglycemia suppressing agent containing a concentrated extract of fermentation product of wheats or barleys as an active ingredient (Patent document 12) and so forth.

Furthermore, as techniques of using a triterpene glycoside as an active ingredient, for example, an agent for preventing diabetes mellitus containing a glycoside extracted from *Gymnema inodorum* as an active ingredient (Patent document 13), a metabolism improving method and a composition therefor containing corosolic acid extracted from banaba as an active ingredient (Patent document 14), a lipase inhibitor (Patent document 15) and a triterpene derivative having an immunosuppressing activity (Patent document 16) have been disclosed.

Furthermore, it has been disclosed that the insulin action enhancing activity of a compound having a lanostane skeleton or 3,4-secolanostane skeleton (Patent document 17) enhances the insulin action in regulation of adipocyte differentiation, although the effect thereof on diseases in the pancreas is unknown.

Furthermore, compounds selected from the group consisting of 24-alkylcholesten-3-ones and 24-alkylcholestan-3-ones that have no double bond in the basic steroid skeleton have been disclosed as hypoglycemic agents (Patent document 18).

As for a substance having a similar structure, a glycoside having a 4-methylstigmast-7-en-3-ol skeleton, it has been reported that 3-O-β-D-glucopyranosyl-4-methylstigmast-7-en-3-ol is contained in Bryony (*Bryonia alba*), a plant of the family Cucurbitaceae (Non-patent document 9). However, this is not a plant that has been generally eaten, and no total synthesis thereof has been reported.

[Patent document 1] International Patent Application Unexamined Publication in Japanese (Kohyo) No. 2001-520019
[Patent document 2] Japanese Patent Laid-open (Kokai) No. 08-208495
[Patent document 3] Japanese Patent Laid-open No. 10-120576
[Patent document 4] Japanese Patent Laid-open No. 10-045604
[Patent document 5] Japanese Patent Laid-open No. 10-036271
[Patent document 6] Japanese Patent Laid-open No. 09-059298
[Patent document 7] Japanese Patent Laid-open No. 60-214741
[Patent document 8] Japanese Patent Laid-open No. 2003-286185
[Patent document 9] U.S. Pat. No. 4,598,069
[Patent document 10] U.S. Patent Application Publication No. 2003/0207818
[Patent document 11] Japanese Patent Laid-open No. 2003-095941
[Patent document 12] Japanese Patent Laid-open No. 2002-371003
[Patent document 13] Japanese Patent Laid-open No. 05-247086
[Patent document 14] Japanese Patent Laid-open No. 2002-205949
[Patent document 15] Japanese Patent Laid-open No. 09-040689
[Patent document 16] International Patent Application Unexamined Publication in Japanese No. 11-511482
[Patent document 17] Japanese Patent Laid-open No. 10-330266
[Patent document 18] Japanese Patent Laid-open No. 2003-048837
[Non-patent document 1] Chem. Pharm. Bull., pp. 624-626, 1993
[Non-patent document 2] Biochemica Biophysica Acta, pp. 63-88, 2000
[Non-patent document 3] Phytomedicine, Vol. 3, pp. 245-248, 1996
[Non-patent document 4] Phytotherapy Research, Vol. 15, pp. 157-161, 2001
[Non-patent document 5] Phytotherapy Research, Vol. 7, pp. 37-42, 1993
[Non-patent document 6] Nippon Rinsho, No. 748, Vol. 1, pp. 615-617, 1999
[Non-patent document 7] Nippon Rinsho, No. 808, Vol. 2, pp. 405-409, 2002
[Non-patent document 8] Yazaki Y. & Muramatsu M. Ed., "Front Line of Diabetes Mellitus", pp. 126-139, Yodosha, 1997
[Non-patent document 9] Khimiya Prirodnykh Soedinenii, Vol. 3, USSR, 1977

SUMMARY OF THE INVENTION

An object of the present invention is to provide a novel compound that can be safely ingested without causing acute hypoglycemia and has a long-term blood glucose level control action to decrease the hemoglobin A1c level. Another object of the present invention is to develop a method for producing a composition that does not contain industrially unfavorable ingredients and contains an effective amount of the compound from a raw material that can be taken safely from experiential viewpoint for food and is readily obtained.

The inventors of the present invention assiduously studied in order to achieve the foregoing objects. As a result, they found that 3-O-β-O-D-glucopyranosyl-4-methylergost-7-en-3-ol, a novel glycoside extracted and purified from mesophyll (clear gel portion) of Aloe vera (*Aloe barbadensis Miller*), could be safely ingested without causing acute hypoglycemia and had a long-term blood glucose level control action for decreasing the hemoglobin A1c level. The present invention was accomplished on the basis of the above findings.

That is, the present invention provides a compound having a structure represented by the following chemical formula (1) (hereinafter also referred to as "the compound of the present invention").

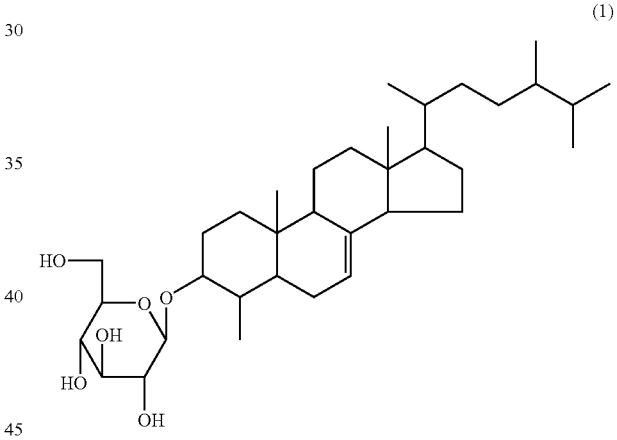

(1)

The present invention also provides a composition containing 0.001% by dry mass or more of the compound of the present invention (hereinafter also referred to as "the composition of the present invention"). The composition of the present invention is preferably an extract of a plant of the family Liliaceae or a fraction thereof, and according to a particularly preferred embodiment, the plant of the family Liliaceae is Aloe vera (*Aloe barbadensis Miller*).

The present invention further provides a hyperglycemia improving agent containing the compound or the composition of the present invention as an active ingredient (hereinafter also referred to as "the drug of the present invention").

The present invention also provides a drug or food or drink containing the aforementioned hyperglycemia improving agent.

The present invention also provides food or drink containing the compound of the present invention or the composition of the present invention as an active ingredient, having a hyperglycemia improving effect, and attached with an indication that the food or drink is used for improvement of hyperglycemia.

Hereinafter, the aforementioned drug and food or drink may be generically referred to as "the drug, food or drink of the present invention."

The present invention further provides a method for producing the compound of the present invention or the composition of the present invention, which comprises extracting a fraction containing the compound from a plant of the family Liliaceae containing the compound, a part thereof or a disruption product thereof by using an organic solvent or hot water and concentrating the fraction, and according to a particularly preferred embodiment, the plant of the family Liliaceae is *Aloe vera* (*Aloe barbadensis Miller*).

The present invention further provides use of the compound of the present invention or a composition containing the same in the production of a drug for improving hyperglycemia. In the use of the present invention, the aforementioned composition is preferably an extract of a plant of the family Liliaceae or a fraction thereof containing 0.001% by dry mass or more of the aforementioned compound, and according to a particularly preferred embodiment, the plant of the family Liliaceae is *Aloe vera* (*Aloe barbadensis Miller*).

The present invention further provides a method for improving hyperglycemia, which comprises administering the compound of the present invention or a composition containing the same to a subject whose hyperglycemia is to be improved. In the method of the present invention, the aforementioned composition is preferably an extract of a plant of the family Liliaceae or a fraction thereof containing 0.001% by dry mass or more of the aforementioned compound, and according to a particularly preferred embodiment, the plant of the family Liliaceae is *Aloe vera* (*Aloe barbadensis Miller*).

BEST MODE FOR CARRYING OUT THE INVENTION

Figure 1:
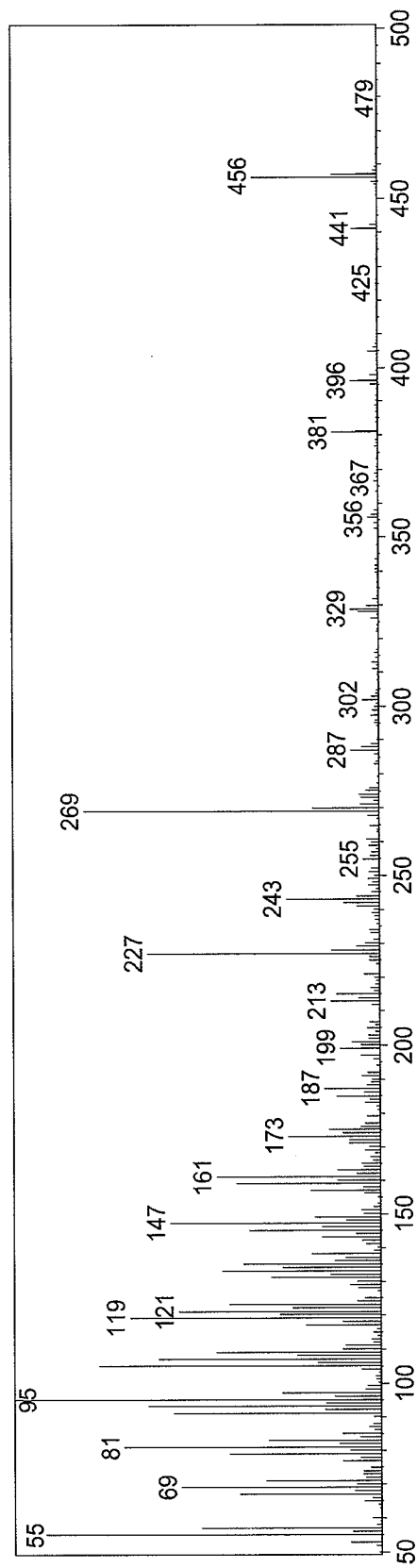
FIG. 1 shows a GC-MS spectrum of the acetylated aglycon moiety of the glycoside of the present invention (photo to replace drawing: a half-tone image shown on a display).

Hereafter, preferred embodiments of the present invention will be explained in detail. However, the present invention is not limited to the following preferred embodiments and can be freely modified within the scope of the present invention.

The compound of the present invention is a compound having a structure represented by the aforementioned chemical formula (1), that is, 3-O-β-D-glucopyranosyl-4-methylergost-7-en-3-ol. That is, the compound of the present invention has a structure formed by dehydration condensation of the hydroxyl group at the 3-position of 4-methylergost-7-en-3-ol and the hydroxyl group at the 1-position of D-glucose.

Furthermore, the composition of the present invention is an extract from a plant of the family Liliaceae or a fraction thereof containing 0.001% by dry mass or more, preferably 0.01% by dry mass or more, more preferably 0.1% by dry mass or more, of the compound of the present invention. The upper limit of the content of the compound of the present invention contained in the composition of the present invention is not particularly limited, and it may be, for example, 50, 70 or 90% by mass.

The compound of the present invention or a composition containing the same can be produced by, for example, extracting a fraction containing the compound of the present invention from a plant belonging to the family Liliaceae and containing the compound of the present invention, a part thereof, or a disruption product thereof by using an organic solvent or hot water and concentrating the fraction.

Examples of the aforementioned plant belonging to the family Liliaceae include plants belonging to the genus *Aloe* or *Allium*. Examples of the plants of the genus Aloe include *Aloe barbadensis Miller*, *Aloe ferox Miller*, *Aloe africana Miller*, *Aloe arborescen Miller* var. *natalensis Berger*, *Aloe spicata Baker* and so forth. In the production of the compound of the present invention or a composition containing the same, although the whole of the aforementioned plant may be used, it is preferable to use mesophyll (clear gel portion) thereof. Such a plant or a part thereof is disrupted preferably by using a homogenizer or the like and thereby liquefied, and the disruption product is extracted by using an organic solvent or hot water. Examples of the organic solvent include alcohols such as methanol, ethanol and butanol; esters such as methyl acetate, ethyl acetate, propyl acetate and butyl acetate; ketones such as acetone and methyl isobutyl ketone; ethers such as diethyl ether and petroleum ether; hydrocarbons such as hexane, cyclohexane, toluene and benzene; halogenated hydrocarbons such as carbon tetrachloride, dichloromethane and chloroform; heterocyclic compounds such as pyridine; glycols such as ethylene glycol; polyhydric alcohols such as polyethylene glycol; nitrile solvents such as acetonitrile, mixtures of these solvents and so forth. Furthermore, these solvents may be anhydrous or hydrous. Among these solvents, ethyl acetate/butanol mixture (3:1) and chloroform/methanol mixture (2:1) are particularly preferred.

As the extraction method, a method used for usual extraction of a plant component can be used. Usually used is, for example, a method of refluxing 1 to 300 parts by mass of an organic solvent with 1 part by mass of fresh plant or dried plant with heating at a temperature at or below the boiling point of the solvent and stirring or shaking, or a method of performing extraction by ultrasonication at room temperature. By isolating insoluble matters from the extraction liquor using a suitable method such as filtration or centrifugation, a crude extract can be obtained.

The crude extract can be purified by various types of chromatography such as normal or reverse phase silica gel column chromatography. When a gradient of chloroform/methanol mixture is used in normal phase silica gel column chromatography as an elution solvent, the compound of the present invention is eluted with a mixing ratio of chloroform:methanol=about 5:1. Furthermore, when a gradient of methanol/water mixture is used in reverse phase silica gel column chromatography as an elution solvent, the compound of the present invention is eluted with methanol of a concentration of about 95%.

The obtained fraction can be further purified by HPLC or the like.

Whether the compound or composition containing the same obtained as described above actually contains the compound of the present invention can be confirmed by, for example, the methods shown in the examples described later. Whether the compound is a glycoside bound with glucose at the aglycon moiety, or whether the aglycon moiety is 4-methylergost-7-en-3-ol can be confirmed by, for example, $^{13}$C-NMR or the like.

The compound of the present invention can also be produced by condensing D-glucose and 4-methylergost-7-en-3-ol. 4-Methylergost-7-en-3-ol can be obtained by extracting and purifying it from a plant. D-Glucose and 4-methylergost-7-en-3-ol can be condensed by, for example, a combination of the methods described in Jikken Kagaku Koza (Lecture of Experimental Chemistry), 4th edition, vol. 26, 1992 (described in p. 272, p. 297 and p. 342). That is, D-glucose is completely acetylated, and then the anomeric position is converted to α-bromide. Then, 4-methylergost-7-en-3-ol is reacted with α-bromide in diethyl ether to attain β-glycosylation, and thereafter the acetyl group is hydrolyzed in a sodium methoxide/methanol mixture to obtain the objective compound.

The compound of the present invention has an action of lowering the hemoglobin A1c level, and as a result, it can control the blood glucose level over a long period of time. Therefore, it can be used as an active ingredient of a hyperglycemia improving agent.

Furthermore, because leaf-skin of *Aloe vera* contains barbaloin and aloe-emodin having a laxative action, it is conventionally considered to be unfavorable as a drug, food or drink for which laxative action is not expected. On the other hand, the composition of the present invention according to a preferred embodiment can be obtained by extraction and fractionation from mesophyll (clear gel portion) of *Aloe vera*, which can be safely ingested from experiential viewpoint for food, and therefore it does not contain barbaloin or aloe-emodin, but contains an effective amount of the compound of the present invention. Therefore, the composition of the present invention is also preferred as an active ingredient of a hyperglycemia improving agent.

The compound or composition of the present invention can be utilized as an active ingredient of the drug, food or drink of the present invention as it is. Furthermore, the composition of the present invention may be a solution and can also be stored and used as powder after it is lyophilized or spray-dried in a conventional manner.

As the drug of the present invention, the compound or the composition of the present invention or those combined with a pharmaceutically acceptable carrier can be orally or parenterally administered to a mammal including human. In the drug of the present invention, the compound of the present invention may be a pharmaceutically acceptable salt. Examples of the pharmaceutically acceptable salt include both metal salts (inorganic salts) and organic salts including, for example, those listed in "Remington's Pharmaceutical Sciences," 17th edition, p. 1418, 1985. Specific examples thereof include, but not limited to, inorganic acid salts such as hydrochloride, sulfate, phosphate, diphosphate, and hydrobromate, and organic acid salts such as malate, maleate, fumarate, tartarate, succinate, citrate, acetate, lactate, methanesulfonate, p-toluenesulfonate, pamoate, salicylate and stearate. Furthermore, the salt may be a salt with a metal such as sodium, potassium, calcium, magnesium and aluminum or a salt with an amino acid such as lysine. Furthermore, solvates such as hydrates of the aforementioned compound or pharmaceutically acceptable salts thereof also fall within the scope of the present invention.

Dosage form of the drug of the present invention is not particularly limited and can be suitably selected depending on the therapeutic purpose. Specific examples thereof include tablet, pill, powder, solution, suspension, emulsion, granules, capsule, syrup, suppository, injection, ointment, patch, eye drop, nasal drop and so forth. For the preparation, additives generally used in usual hyperglycemia improving drugs as pharmaceutical carriers such as excipients, binders, disintegrating agents, lubricants, stabilizers, flavoring agents, diluents, surfactants and solvents for injection can be used. Furthermore, so long as the effect of the present invention is not degraded, the compound or composition of the present invention can be used in combination with other drugs having hyperglycemia improving effect.

Although the amount of the compound or the composition of the present invention contained in the drug of the present invention is not particularly limited and can be suitably selected, the amount may be, for example, 0.001 to 10% by mass, preferably 0.01 to 1% by mass, particularly preferably 0.05 to 1% by mass, in terms of the amount of the compound of the present invention.

The drug of the present invention is useful for a therapeutic or prophylactic treatment of a disease resulted from hyperglycemic conditions such as, for example, diabetes and its associated symptoms and conditions (likelihood of developing diabetes or related conditions). In particular, it can also be used to prevent onset of diabetes mellitus from hyperglycemic conditions.

The drug of the present invention contains the aforementioned agent of the present invention (hyperglycemia improving agent) and is useful for a therapeutic or prophylactic treatment of a disease resulted from hyperglycemic conditions such as diabetes and its associated symptoms and conditions (likelihood of developing diabetes or related conditions). In particular, it can also be used to prevent onset of diabetes mellitus from hyperglycemic conditions. Furthermore, the drug of the present invention can cure or prevent various diseases, complications and so forth resulted from hyperglycemic conditions, and reduce risks of these diseases, complications and so forth.

Examples of such various diseases and complications resulted from hyperglycemic conditions include diabetic retinopathy, diabetic nephropathy, diabetic neuropathy, diabetic gangrene, cerebral apoplexy resulted from diabetes mellitus, myocardial infarction resulted from diabetes mellitus and so forth.

The term "hyperglycemic conditions" refers to conditions that the blood glucose levels are out of the normal ranges, and the normal ranges are generally defined as a fasting blood glucose level of 110 mg/dl or lower, a blood glucose level 1 hour after 75 g glucose load of 160 mg/dl or lower, and a blood glucose level 2 hours after the same glucose load of 120 mg/dl or lower (Nihon Rinsho, No. 806, Vol. 1, pp. 28-35, 2002). Furthermore, the drug of the present invention is preferably used for a treatment of a patient with a hemoglobin A1c level higher than normal, for example, a hemoglobin A1c level of 5.8% or higher.

The administration time of the agent or drug of the present invention is not particularly limited and can be suitably selected according to the method for treating an objective disease. Furthermore, the administration route is preferably determined depending on the dosage form, age, sex and other conditions of patients, severity of symptoms of patients and so forth.

The dose of the active ingredient in the agent of the present invention is suitably selected depending on the dosing regimen, age, sex, severity of disease, other conditions of patients and so forth. The amount of the compound of the present invention as an active ingredient is usually selected from the range of, preferably 0.01 to 10 mg/kg/day, more preferably 0.1 to 1 mg/kg/day, as a tentative dose. Furthermore, when the composition of the present invention is used, the dry weight of the composition is selected from the range of, preferably 0.1 to 1000 mg/kg/day, more preferably 1 to 100 mg/kg/day, as a tentative amount. In any case, the dose can be ingested once daily or several times as divided portions.

The agent or drug of the present invention or the active ingredient thereof, i.e., the compound or the composition of the present invention, can be added to food or drink. The form and property of the food or drink are not particularly limited so long as the effect of the active ingredient is not degraded, and the food or drink can be orally ingested, and it can be produced in a conventional manner by using raw materials usually used for food or drink except that the aforementioned active ingredient is added.

The amount of the compound or the composition of the present invention contained in the food or drink of the present invention is not particularly limited and can be suitably selected. For example, the compound or the composition of the present invention is contained in food or drink in an amount of 0.0001 to 1% by mass, preferably 0.001 to 1% by mass, particularly preferably 0.005 to 1% by mass, in terms of the amount of the compound of the present invention.

The food or drink of the present invention can be used for various applications utilizing the hyperglycemia improving effect. For example, it can be used as food or drink suitable for those who are getting concerned about their blood glucose levels, food or drink useful for decreasing or eliminating risk factors of lifestyle-related diseases such as diabetes mellitus.

As for the food or drink of the present invention, the expression "improvement of hyperglycemia" means that improvement or prevention of various health damages resulted from hyperglycemia, and "prevention of hyperglycemia," "suppression of increase in blood glucose level," "improvement of increase in blood glucose level," "prevention of increase in blood glucose level," "improvement of high hemoglobin A1c level" and so forth are exemplified in the present invention as terms having a meaning similar to that of the aforementioned "improvement of hyperglycemia".

Furthermore, the food or drink of the present invention is useful for a prophylactic treatment of a disease resulted from hyperglycemic conditions such as diabetes mellitus and its associated symptoms and conditions (likelihood of developing diabetes or related conditions). In particular, it can also be used to prevent onset of diabetes mellitus from hyperglycemic conditions. Furthermore, the food or drink of the present invention can be used for a prophylactic treatment of various diseases, complications and so forth resulted from hyperglycemic conditions and can decrease risks of these diseases, complications and so forth.

Examples of such various diseases and complications resulted from hyperglycemic conditions include diabetic retinopathy, diabetic nephropathy, diabetic neuropathy, diabetic gangrane, cerebral apoplexy resulted from diabetes mellitus, myocardial infarction resulted from diabetes mellitus and so forth.

The food or drink of the present invention is preferably marketed as food or drink attached with an indication that the food or drink is used for improving hyperglycemia, for example, "food or drink containing a compound having hyperglycemia improving effect indicated as 'For improving hyperglycemia,'" "food or drink containing a plant extract indicated as 'For improving hyperglycemia,'" "food or drink containing *Aloe vera* extract indicated as 'For improving hyperglycemia'" and so forth.

Because the compound, the composition and others of the present invention have a hyperglycemia improving effect, it is considered that the indication of "improvement of hyperglycemia" also means "suppression of increase in blood glucose level." Therefore, the food or drink of the present invention can be indicated as "For suppressing increase in blood glucose level." That is, the aforementioned indication of "For improvement of hyperglycemia" may be an indication of "For suppression of increase in blood glucose level."

The wording used for such an indication as mentioned above is not necessarily be limited to the expression "For improvement of hyperglycemia" or "For suppression of increase in blood glucose level", and any other wording expressing the effect of improving hyperglycemia or suppressing increase in blood glucose level of course falls within the scope of the present invention. As such a wording, for example, an indication based on various uses allowing consumers to recognize the effect of improving hyperglycemia or suppressing increase in blood glucose level is also possible. Examples include, for example, indications of "Suitable for those who are getting concerned with blood glucose levels", "Useful for decrease or elimination of risks of lifestyle-related diseases such as diabetes mellitus".

The aforementioned term "indication" include all actions for informing consumers the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods, or providing information including those as contents with indicating the aforementioned use by an electromagnetic method (Internet etc.) and so forth.

The indication is preferably an indication approved by the administration etc. (for example, an indication in a form based on an approval, which is qualified on the basis of any of various legal systems provided by the administration), and it is particularly preferably an indication on advertisement materials at the sales spots such as packages, containers, catalogs, pamphlets and POPs, others documents and so forth.

Examples of the indication further include, for example, indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

EXAMPLES

The present invention will be explained more specifically with reference to the following examples. However, the scope of the present invention is not limited to these examples.

Preparation Example 1

Examples of preparation of 3-O-β-D-glucopyranosyl-4-methylergost-7-en-3-ol from *Aloe vera* will be described below.

3-O-β-D-Glucopyranosyl-4-methylergost-7-en-3-ol was extracted from *Aloe vera* and purified as described below.

In an amount of 100 kg of mesophyll (clear gel portion) of *Aloe vera* was liquefied by using a homogenizer, added with 100 L of an ethyl acetate/butanol mixture (3:1) and stirred.

The mixture was left standing overnight to separate the ethyl acetate/butanol mixture and the aqueous layer, and the ethyl acetate/butanol mixture was recovered. The extract from this ethyl acetate/butanol mixture obtained by concentrating the ethyl acetate/butanol mixture under reduced pressure weighed 13.5 g.

Hyperglycemia improving effect was evaluated for the aforementioned aqueous layer and the extract from the ethyl acetate/butanol mixture in diabetes model mice described later, and the effect was observed for the extract from the ethyl acetate/butanol mixture. Therefore, it was attempted to isolate and purify components in the extract. First, the aforementioned extract was examined by thin layer chromatography (Merck Ltd., Silica gel 60F254 and RP-18F2543). As a result, an isolation method based on normal phase silica gel column chromatography using a chloroform/methanol mixture appeared to be suitable. Accordingly, a solution of 13 g of the aforementioned extract dissolved in 1 mL of a chloroform/methanol mixture (1:1) was loaded on a column filled with 400 g of silica gel 60 (Merck Ltd.) to attain adsorption of the components to the column, then the components were eluted with a chloroform/methanol mixture by the stepwise gradient method, in which the methanol concentration was increased stepwise (mixing ratios of chloroform:methanol=100:1, 25:1, 10:1, 5:1 and 1:1), and the eluate was fractionated for each mixing ratio of the aforementioned mixture. The yields of crude purification products obtained from the fractions after removing the solvent were 1.44, 3.0, 1.17, 1.28 and 2.27 g, respectively. It was confirmed by a method using the aforementioned model animals that, among these fractions, an active component existed in the fraction eluted with the mixture of chloroform:methanol=5:1 (crude purification product A). The existence of barbaloin or aloe-emodin was not confirmed by thin layer chromatography analysis.

Furthermore, to isolate and purify the active component from the aforementioned crude purification product A, this crude purification product A was examined by using thin layer chromatography (Merck Ltd., Silica gel 60F254 and RP-18F2543). As a result, an isolation method based on reverse phase silica gel column chromatography using methanol appeared to be suitable. Accordingly, the aforementioned crude purification product A was dissolved in 1 mL of a chloroform/methanol mixture (1:1) and loaded on a column filled with 180 g of COSMOSIL 140 (Nacalai Tesque, Inc.) to attain adsorption of the component to the column. Then, elution was performed by successively using 600 mL of 85% methanol solution, 600 mL of 95% methanol solution and 100 mL of 100% methanol. 3-O-β-D-Glucopyranosyl-4-methylergost-7-en-3-ol was concentrated and isolated in a fraction eluted with 95% methanol and weighed 370 mg after removing the solvent. Hereafter, this product is referred to as compound 1.

Because the compound 1 showed an Rf value very close to that of β-sitosterol glucoside in an examination based on thin layer chromatography, it was anticipated to be a glycoside in which 1 molecule of sugar bound to the aglycon moiety. Furthermore, to examine the sugar composition of the compound 1, the compound 1 was subjected to methanolysis, then made into a TMS derivative and subjected to GC-MS measurement. As a result, in the measurement of the TMS derivative for the sugar portion of the compound 1, it showed main peaks at retention times of 14.28, 14.61 and 16.34 minutes, which were substantially consistent with the retention times of the main peaks of the sample glucose (Nacalai Tesque, Inc.), 14.27, 14.60 and 16.33 minutes. Furthermore, peaks corresponding to the main peaks of the sample galactose (Kishida Chemical Co., Ltd.) and the sample xylose (Kishida Chemical Co., Ltd.) were not observed. Thus, it was confirmed that the type of the sugar contained in the compound 1 was glucose.

From the above results, it was estimated that the compound 1 was a glycoside in which 1 molecule of glucose bound to the aglycon moiety. However, when the compound 1 was measured by $^{13}$C-NMR (125 MHz, CDCl$_3$), the existence of contaminants was confirmed. Therefore, it was considered that further purification should be required to determine its structure. Accordingly, the compound 1 was methanolyzed and then acetylated, and then the structure of the aglycon moiety as well as the binding site of the aglycon moiety and the sugar were confirmed. The method therefor will be described below.

Figure 2:
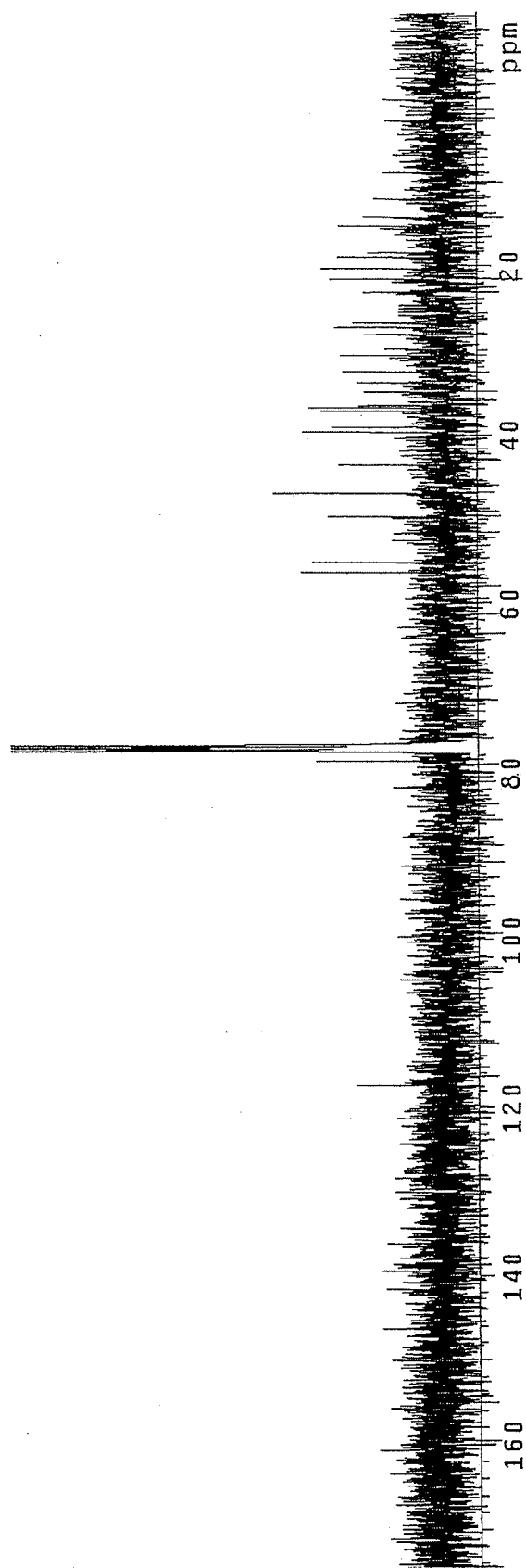
FIG. 2 shows a $^{13}$C-NMR chart of the acetylated aglycon moiety of the glycoside of the present invention (photo to replace drawing: a half-tone image shown on a display).

In an amount of 50 mg of the compound 1 was dissolved in methanol (50 mL) containing 5% hydrochloric acid, refluxed with heating for 6 hours for methanolysis and dried to obtain a residue (about 30 mg). This residue was purified by silica gel column chromatography (hexane:chloroform=9:1) to obtain a compound 2 (10 mg). This compound 2 (5 mg) was added with acetic anhydride and pyridine (2 drops each) and heated at 70° C. for 30 minutes for acetylation, and then the solvent of the reaction mixture was evaporated to obtain a compound 3. The results of the analysis of this compound 3 by GC-MS and $^{13}$C-NMR (125 MHz, CDCl$_3$) are shown in FIGS. 1 and 2, respectively. The measurement conditions and results are as follows. 3-Acetoxy-4-methylergost-7-ene used as a reference substance was prepared by extracting aloe, purifying the extract, confirming the structure of the purified product by $^{13}$C-NMR and acetylating the same.

[$^{13}$C-NMR spectrum (d values, in CDCl$_3$)]; C-1:36.8, C-2: 27.3, C-3:78.7, C-4:37.0, C-5:46.9, C-6:26.8, C-7:117.4, C-8:139.4, C-9:49.7, C-10:34.9, C-11:21.6, C-12:39.7, C-13: 43.6, C-14:55.1, C-15:23.1, C-16:28.2, C-17:56.3, C-18: 12.0, C-19:14.2, C-20:36.5, C-21:19.0, C-22:33.9, C-23: 30.6, C-24:39.1, C-25:32.6, C-26:20.4, C-27:18.4, C-28: 15.6, C-29:15.3

[GC-MS]
Apparatus: GC-17A/GCMS5050A (SHIMADZU)
GC column: NEUTRA BOND-5 (GL Sciences)
Column temperature: 100° C. (2 min)>(10° C./min)>300° C. (28 min)
Injection temperature: 250° C.
Carrier gas: He (1.3 mL/min)
Interface temperature: 300° C.
MS mode: EI
Ionization energy: 70 eV

[Results]
Reference substance: 3-acetoxy-4-methylergost-7-ene: tR [min]=39.4; m/z 456 [M]$^+$, 441 [M-CH$_3$]$^+$, 396 [M-AcOH]$^+$, 381 [M-CH$_3$—AcOH]$^+$ Compound 3: tR [min]=39.2; m/z 456 [M]$^+$, 441 [M-CH$_3$]$^+$, 396 [M-AcOH]$^+$, 381 [M-CH$_3$—AcOH]$^+$ The results of the NMR measurement of the compound 3 were consistent with the values of 3-acetoxy-4-methylergost-7-ene shown in a literature (Yukagaku (Oil Chemistry), Vol. 36, No. 5, pp. 301-319, 1987). These results revealed that the compound 2 was 4-methylergost-7-en-3-ol. Furthermore, as a result of FAB-MS measurement, the molecular weight of the compound 1 was found to be 576. When the compound 2 (aglycon moiety) and glucose were condensed, the molecular weight of the obtained compound was 414 (compound 2)+180 (glucose)−18 (water)=576, which was consistent with the molecular weight of the compound 1.

The above results revealed that the compound 1 had a structure of 3-O-β-D-glucopyranosyl-4-methylergost-7-en-3-ol.

The molecular formulas, molecular weights and chemical formulas of the compounds are shown below.

(Compound 1)
Molecular formula: $C_{35}H_{60}O_6$
Molecular weight: 576
Chemical formula: The following chemical formula (1)

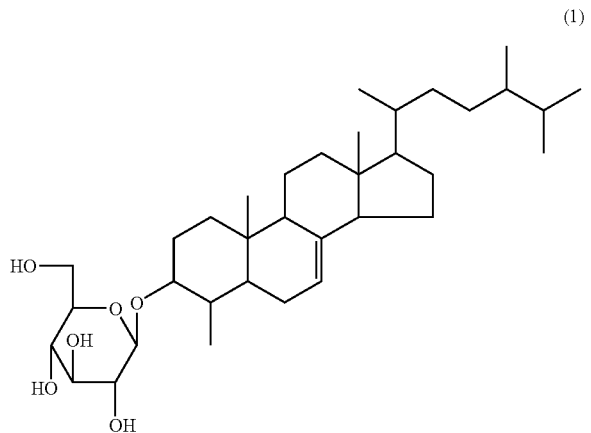

(1)

(Compound 2)
Molecular formula: $C_{29}H_{50}O$
Molecular weight: 414
Chemical formula: The following chemical formula (2)

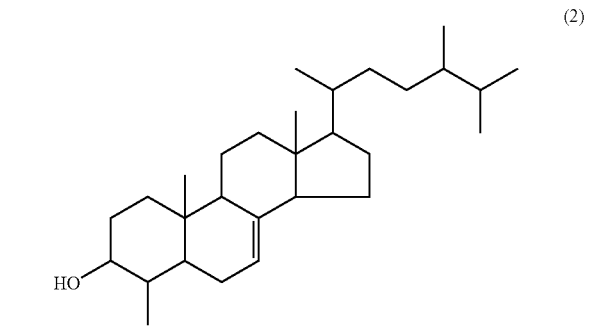 [SMILES: CC(C)C(C)CCC(C)C1CCC2C3=CCC4C(C)C(O)CCC4(C)C3CCC21C]

(2)

(Compound 3)
Molecular formula: $C_{31}H_{52}O_2$
Molecular weight: 456
Chemical formula: The following chemical formula (3)

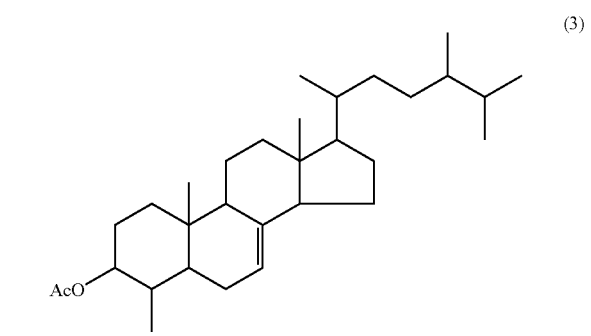 [SMILES: CC(=O)OC1CCC2(C)C3CCC4(C)C(CCC4C(C)CCC(C)C(C)C)C3=CCC2C1C]

(3)

Preparation Example 2

Mesophyll (clear gel portion) of *Aloe vera* was dried by heating, 0.3 g of disrupted dry *Aloe vera* powder was added with 60 mL of 60, 80 or 100% ethanol and refluxed by heating at 60° C. for 1 hour. The extract was centrifuged at 1500 rpm for 20 minutes, and the supernatant was concentrated under reduced pressure to completely remove ethanol and thereby obtain a crude extract. The dry weights of the crude extracts obtained by extraction using 60, 80 and 100% ethanol were 65, 42 and 18 mg, respectively. It was confirmed by thin layer chromatography that these crude extracts contained 3-O-β-D-glucopyranosyl-4-methylergost-7-en-3-ol.

Preparation Example 3

Mesophyll (clear gel portion) of *Aloe vera* was dried by heating, 0.3 g of dry crushed *Aloe vera* powder was added with 60 mL of water and refluxed by heating at 95° C. for 5 hours. The extract was centrifuged at 1500 rpm for 20 minutes, and the supernatant was lyophilized to obtain 75 mg of a crude extract. It was confirmed by thin layer chromatography that this crude extract contained 3-O-β-D-glucopyranosyl-4-methylergost-7-en-3-ol.

Preparation Example 4

Mesophyll (clear gel portion) of *Aloe vera* was dried by heating, disrupted and dried, 21 kg of *Aloe vera* powder thus prepared was added with 90 L of a chloroform/methanol mixture (2:1), then immersed overnight in the mixture at room temperature and collected by filtration, and the residue obtained by the filtration was added with 90 L of chloroform/methanol mixture (2:1) again. This procedure was repeated 4 times in total. The obtained filtrate (350 L) was concentrated at 28° C. to finally obtain 784 g of a crude extract. In an amount of 780 g of this crude extract was added with 2 L of a chloroform/methanol mixture (2:1), stirred for 1 hour and filtered to recover the chloroform/methanol mixture layer (A). The residue obtained by the filtration was successively added with 2.5 L of water and 2 L of ethyl acetate and stirred for 1 hour, and the ethyl acetate layer (B) was recovered. The remaining aqueous layer was added with 5 L of chloroform again and stirred for 1 hour, and the chloroform layer (C) was recovered.

The recovered organic solvent extracts A, B and C were mixed, concentrated at 23° C. and loaded on a silica gel column [glass column, 52 mm×350 mm, packed material: IR-63/210-W (Daiso Co., Ltd.)]. Subsequently, while monitoring the eluate by thin layer chromatography, 10 L of a hexane/chloroform mixture (1:1), 10 L of chloroform, 20 L of a chloroform/methanol mixture (10:1) and 20 L of a chloroform/methanol mixture (5:1) were passed through the column in this order, and a fraction 1 (about 1 L), fraction 2 (about 1.5 L), fraction 3 (about 1.5 L) and fraction 4 (about 1.5 L) were recovered in the order of the used elution solvents.

It was confirmed by thin layer chromatography that, among these, the fraction 3 contained the objective glycoside, and then the solvent of the fraction 3 was removed to obtain 131.6 g of a crude extract. In an amount of 130 g of this crude extract was loaded on a silica gel column [glass column, 70 mm×500 mm, packed material: SP-60-40/60 (Daiso Co., Ltd.)] again and eluted successively with 10 L of a chloroform/methanol mixture (30:1), 50 L of a chloroform/methanol mixture (20:1), 10 L of a chloroform/methanol mixture (10:1) and 10 L of a chloroform/methanol mixture (1:1) as elution solvents under conditions of a pressure of 10 kgf·cm$^{-2}$ and a flow rate of 40 mL/min. The eluates were fractionated as 100-mL fractions by using a fraction collector to collect fractions 1 to 8.

The collected fractions were examined by thin layer chromatography, and as a result, it was revealed that the objective glycoside and contaminants existed in the fraction 7. Therefore, this fraction was concentrated, loaded on a silica gel column [glass column, 70 mm×500 mm, packed material: SP-60-40/60 (Daiso Co., Ltd.)] again, and successively eluted with 10 L of a chloroform/methanol mixture (20:1) and 10 L of a chloroform/methanol mixture (10:1) as elution solvents under conditions of a pressure of 10 kgf·cm$^{-2}$ and a flow rate of 40 mL/min. As a result, 25.3 g of 3-O-β-D-glucopyranosyl-4-methylergost-7-en-3-ol was prepared, which was the objective glycoside contained in the elution fraction of the chloroform/methanol mixture (10:1).

Test Example 1

This test was performed in order to evaluate the hyperglycemic condition improving effect of 3-O-β-D-glucopyranosyl-4-methylergost-7-en-3-ol.

(1) Preparation of Sample

The 3-O-β-D-glucopyranosyl-4-methylergost-7-en-3-ol produced in Preparation Example 1 mentioned above was used as a test sample.

(2) Test Method

As type-II diabetes model mice, 6-week old male db/db mice (purchased from Clea Japan, Inc.) were used. These mice were divided into groups, each consisting of 7 animals. The test sample was dissolved in DMSO, and the concentration of 3-O-β-D-glucopyranosyl-4-methylergost-7-en-3-ol was adjusted to 15 μg/mL with physiological saline. The final DMSO concentration was adjusted to 0.2%. The type-II diabetes model mice were orally administered 1 mL of the test sample solution once a day everyday with a sonde. A solution that did not contain the test sample was used as a negative sample. Fasting blood glucose levels and random blood glucose levels were measured over time using Antisense II (Bayer-Sankyo Co., Ltd.). The fasting blood glucose levels were measured after 15 hours of fasting.

(3) Hyperglycemia Improving Effect

Figure 3:
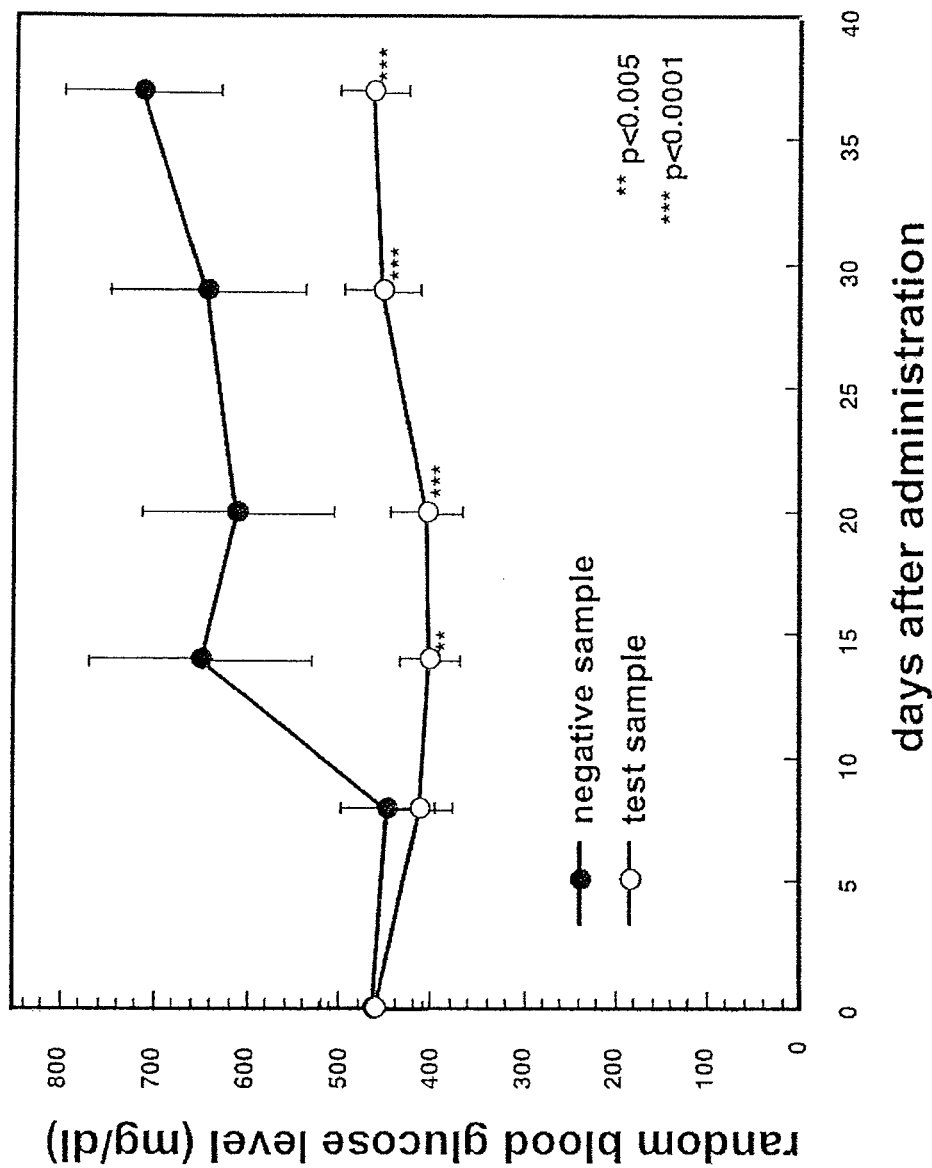
FIG. 3 shows a graph showing changes over time in random blood glucose levels of mice administered with the compound of the present invention.
Figure 4:
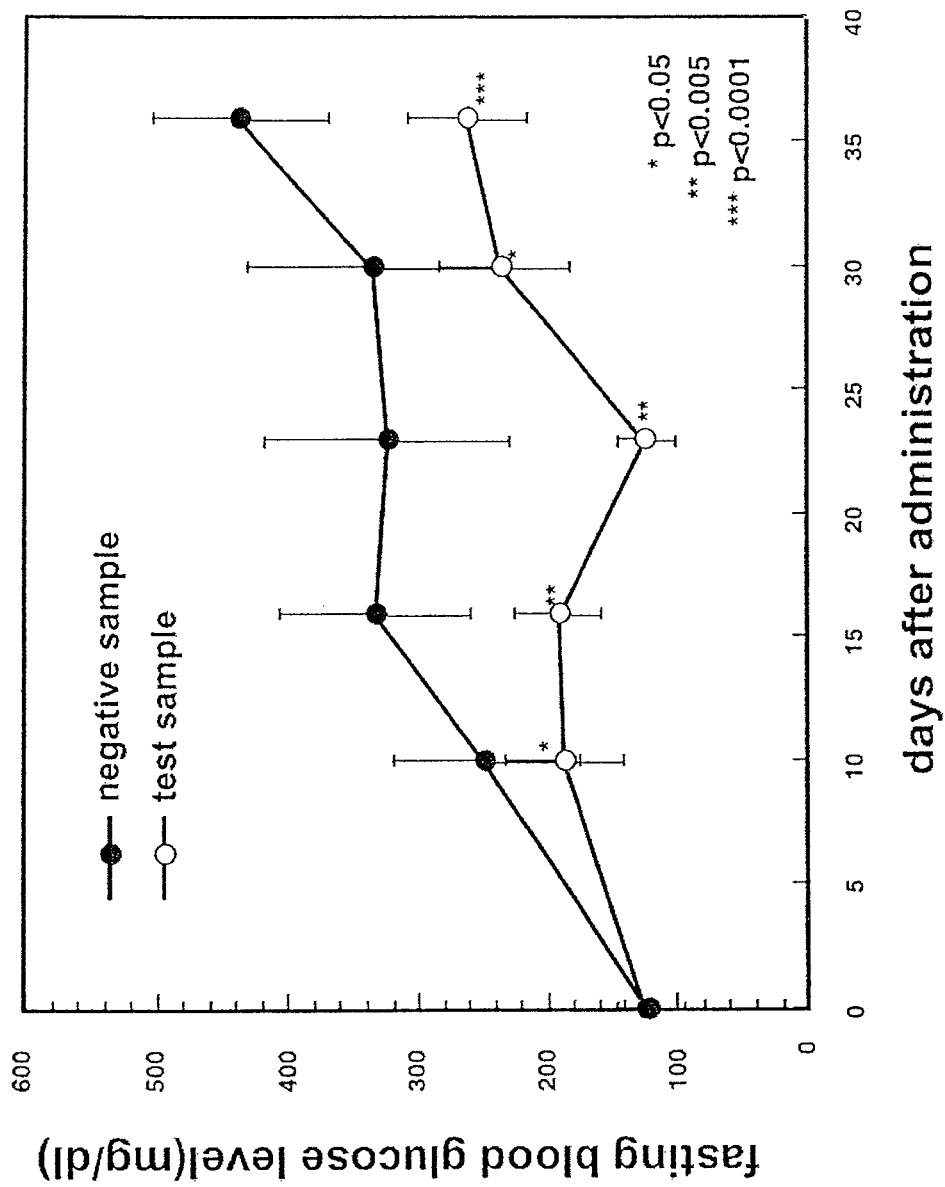
FIG. 4 shows a graph showing changes over time in fasting blood glucose levels of mice administered with the compound of the present invention.

Changes over time in random blood glucose levels and fasting blood glucose levels during the test sample administration period are shown in FIGS. 3 and 4. In the mice administered with the negative sample, rapid increase were observed in both the random blood glucose levels and fasting blood glucose levels, whereas effect of suppressing the increases in blood glucose levels was clearly observed in the mice repeatedly administered with the test sample.

Test Example 2

This test was performed in order to evaluate the hemoglobin A1c lowering action of 3-O-β-D-glucopyranosyl-4-methylergost-7-en-3-ol.

(1) Preparation of Sample

The 3-O-β-D-glucopyranosyl-4-methylergost-7-en-3-ol produced in Preparation Example 1 mentioned above was used as a test sample.

(2) Test Method

As type-II diabetes model mice, 6-week old male db/db mice (purchased from Clea Japan, Inc.) were used. These mice were divided into groups, each consisting of 7 animals. The test sample was dissolved in DMSO, and the concentration of 3-O-β-D-glucopyranosyl-4-methylergost-7-en-3-ol was adjusted to 1, 5 and 15 μg/mL with physiological saline. The final DMSO concentration was adjusted to 0.2%. The type-II diabetes model mice were orally administered with 1 mL of the test sample solution once day everyday with a sonde. A solution that did not contain the test sample was used as a negative sample. On the 35th day from the start of the administration, hemoglobin A1c levels were measured by using DCA 2000 (Bayer-Sankyo Co., Ltd.).

(3) Hemoglobin A1c Lowering Action

The measurement results of hemoglobin A1c levels on the 35th day from the start of the administration are shown in Table 1. In comparison with the hemoglobin A1c levels after administration of the negative sample, statistically significant decreases in the hemoglobin A1c levels were observed after the repetitive administration of 5 or 15 μg of the test sample, indicating existence of blood glucose level control effect over a long period of time. Further, during the administration period, there was no case showing adverse side effect symptoms or acute hypoglycemic conditions after the administration, and no abnormality was observed in body weight and pathological findings.

TABLE 1

| Samples | Hemoglobin A1c relative levels (%) 35th day from the administration | p value |
|---|---|---|
| Test sample (1 μg) | 98.6 ± 7.3 | |
| Test sample (5 μg) | 89.6 ± 7.9* | 0.017 |
| Test sample (15 μg) | 73.5 ± 8.6* | 0.00001 |
| negative sample | 100 | |

*statistical significance was observed.

Test Example 3

This test was performed in order to examine the hemoglobin A1c lowering action and the dose of the extracted crude purification product A containing 3-O-β-D-glucopyranosyl-4-methylergost-7-en-3-ol derived from Aloe vera.

(1) Preparation of Sample

The extracted crude purification product A containing 3-O-β-D-glucopyranosyl-4-methylergost-7-en-3-ol produced in Preparation Example 1 mentioned above was used.

(2) Test Method

As type-II diabetes model mice, 6-week old male db/db mice (purchased from Clea Japan, Inc.) were used. These mice were divided into groups, each consisting of 7 animals. The test sample was dissolved in DMSO, and the concentration of the extracted crude purification product A was adjusted to 25, 100 and 200 μg/mL with physiological saline. The final DMSO concentration was adjusted to 0.2%. The type-II diabetes model mice were orally administered with 1 mL of the test sample solution once a day everyday with a sonde. A solution that did not contain the test sample was used as a negative sample. On the 35th day from the start of the administration, hemoglobin A1c levels were measured by using DCA 2000 (Bayer-Sankyo Co., Ltd.).

(3) Blood Glucose Level and Hemoglobin A1c Level

The measurement results of hemoglobin A1c levels on the 35th day from the start of the administration are shown in Table 2. In comparison with the hemoglobin A1c level of the negative test, decreases in the hemoglobin A1c level were observed after repetitive administration of 100 or 200 μg of the test sample, and thus existence of blood glucose level control effect over a long period of time was statistically significantly demonstrated. Further, during the administration period, there was no case showing adverse side effect symptoms or acute hypoglycemic conditions after administration, and no abnormality was observed in body weight and pathological findings.

TABLE 2

| Samples | Hemoglobin A1c relative levels (%) 35th day from the administration | p value |
|---|---|---|
| Test sample (crude purification product 25 μg) | 92.5 ± 7.1 | 0.1571 |
| Test sample (crude purification product 100 μg) | 84.9 ± 8.2* | 0.0275 |
| Test sample (crude purification product 200 μg) | 82.0 ± 8.6* | 0.0129 |
| negative sample | 100 | |

*statistical significance was observed.

The compound of the present invention can be safely administered or ingested without causing acute hypoglycemia and has a long-term blood glucose level control action lowering the hemoglobin A1c level. Further, the composition of the present invention can be produced by using a plant of the family Liliaceae, a plant that can be safely ingested from experiential viewpoint for food and is readily available, for example, a plant of the genus *Aloe* or *Allium*. Further, the composition of the present invention contains an effective amount of the compound of the present invention, and in a preferred embodiment thereof, it does not contain barbaloin or aloe-emodin, which are unfavorable components as a drug, food or drink.

What is claimed is:

1. A method for producing a purified compound having a structure represented by the following chemical formula (1) or a composition containing the purified compound, wherein the method comprises extracting the clear gel portion of mesophyll of a plant of the genus *Aloe* with an acetate/butanol mixture or a chloroform/methanol mixture to obtain a fraction and concentrating the fraction to obtain the purified compound having a structure represented by the following chemical formula structure (1):

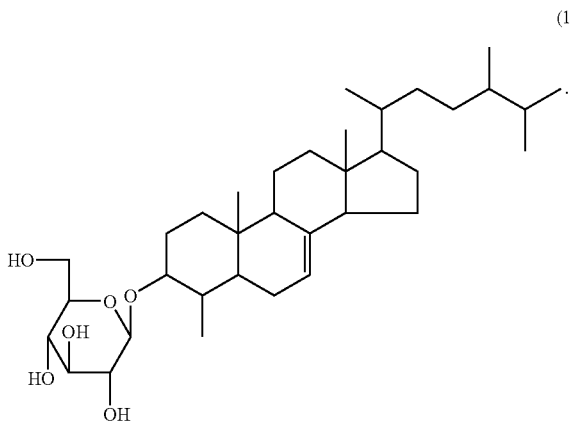

(1)

2. The method according to claim 1, wherein the plant of the genus *Aloe* is *Aloe barbadensis Miller* or *Aloe arborescen Miller* var. *natalensis Berger*.

3. A method for the production of a drug for improving hyperglycemia which comprises mixing the purified compound having a structure represented by the chemical formula structure (1) of claim 1 or a composition containing the purified compound with a pharmaceutically acceptable carrier, wherein the drug contains 0.001% by mass of the compound:

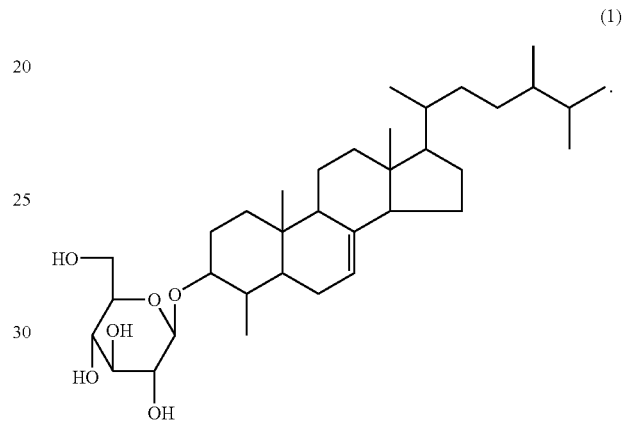

(1)

* * * * *